United States Patent
Kim et al.

(10) Patent No.: US 7,460,227 B1
(45) Date of Patent: Dec. 2, 2008

(54) METHOD TO DETECT BONE FRAGMENTS DURING THE PROCESSING OF MEAT OR FISH

(75) Inventors: Moon S. Kim, Silver Spring, MD (US); Alan M. Lefcourt, Elkridge, MD (US); Yud-Ren Chen, Laurel, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 331 days.

(21) Appl. No.: 11/304,283

(22) Filed: Dec. 15, 2005

Related U.S. Application Data

(60) Provisional application No. 60/640,339, filed on Dec. 30, 2004.

(51) Int. Cl.
 *G01J 3/30* (2006.01)
(52) U.S. Cl. .................................. 356/317; 250/459.1
(58) Field of Classification Search ................ 356/317; 426/231
 See application file for complete search history.

(56) References Cited

U.S. PATENT DOCUMENTS

| | | | |
|---|---|---|---|
| 4,631,413 A * | 12/1986 | Jensen et al. | 250/458.1 |
| 5,428,657 A * | 6/1995 | Papanicolopoulos et al. | 378/86 |
| 5,847,382 A * | 12/1998 | Koch et al. | 250/223 R |
| 5,902,177 A * | 5/1999 | Tessier et al. | 452/156 |
| 6,808,448 B1 * | 10/2004 | Kanaya et al. | 452/2 |

OTHER PUBLICATIONS

Kim et al., "Multispectral laser-induced fluorescence imaging system for large biological animals", Jul. 1, 2003, Applied Optics, vol. 42, No. 19, pp. 3927-3934.*

Kim, Moon S., et al., "Optimal Fluorescence Excitation and Emission Bands for Detection of Fecal Contamination", Journal of Food Protection, vol. 66, No. 7, 2003, pp. 1198-1207.

* cited by examiner

*Primary Examiner*—Kara E Geisel
(74) *Attorney, Agent, or Firm*—Randall E. Deck; John Fado; Lesley Shaw

(57) ABSTRACT

Bones, bone fragments, and shell fragments on or near the surface of processed animal flesh may be detected by detecting their fluorescent emissions. The surface of the flesh is illuminated with UV or visible light to elicit fluorescence of animal bones or shells, and the fluorescent light emissions are measured at first and second different wavelengths, which wavelengths are selected to yield a substantial difference between the ratio or subtractive difference for bones or shells and the ratio or subtractive difference for animal flesh. The ratio and/or subtractive difference of the fluorescent light emissions at the first and second wavelengths is calculated, and the presence of bone, bone fragment, or shell fragment is determined therefrom.

22 Claims, 9 Drawing Sheets

Bone Fragments

METHOD TO DETECT BONE FRAGMENTS DURING THE PROCESSING OF MEAT OR FISH

This application hereby claims the benefit of U.S. provisional patent application 60/640,339, filed Dec. 30, 2004, the content of which are incorporated by reference herein.

BACKGROUND OF THE INVENTION

1. Field of the Invention

The invention relates to an improved method and apparatus for detecting bone fragments near the surface of processed meat or fish.

2. Description of the Prior Art

Food products prepared from ground or diced animal flesh, particularly from poultry, cattle, swine, fish, and shellfish, enjoy widespread consumption throughout the United States and the world. However, during the de-bonding or shelling operations in the preparation of these products, bones, bone fragments, and shell fragments may fail to be completely removed from the flesh. Manual detection of these contaminants is not only tedious and costly, but may be subject to human error.

X-ray detection of bones, bone fragments, and shell fragments has been proposed, but this system too is costly, and is not suitable for rapid on-line operations.

Jensen et al. (U.S. Pat. No. 4,631,413) disclosed that bone fragments, fat, cartilage, and connective tissue may be detected in food products by fluorescence. Specifically, the patent disclosed illuminating the product with light having a wavelength of about 325 to 360 nm, and examining the emission of any fluorescence. Emission wavelengths centered at 455 and 475 nm were disclosed as being particularly useful for detection of bones.

However, despite these advances, there exists a continuing need for a high-speed system for detecting bones, bone fragments, and shell fragments in animal flesh with increased sensitivity and accuracy.

SUMMARY OF THE INVENTION

We have now invented a novel and improved method for detecting bone, bone fragment, and shell fragment contaminants on or near the surface of animal flesh during processing using fluorescent spectroscopy. In this process, the surface of the product is illuminated with UV or visible light having a wavelength effective to elicit fluorescence of animal bones or shells. The fluorescent light emissions are measured at first and second different wavelengths which are selected to yield a substantial difference between the ratio or subtractive difference for bones or shells and the corresponding ratio or subtractive difference for animal flesh, wherein the ratio is the ratio of the fluorescent light emission intensities measured at the first and second wavelengths, and the subtractive difference is the quantitative difference between the fluorescent light emission intensities measured at the first and second wavelengths. The ratio and/or subtractive difference of the fluorescent light emissions at the first and second wavelengths is calculated, and the presence of bones, bone fragments, or shell fragments is determined therefrom.

In accordance with this discovery, it is an object of this invention to provide an improved method for detecting the presence of bones, bone fragments, and shell fragments on or near the surface of an animal flesh product.

Another object of the invention is to provide an improved high-speed method which is capable of near real time detection of bones, bone fragments, and shell fragments on or near the surface of an animal flesh product, which could not interfere with existing processing line speeds or procedures.

Yet another object of the invention is to provide an improved method which for the detection of bones, bone fragments, and shell fragments on or near the surface of an animal flesh product with increased sensitivity and accuracy and which is substantially free from non-specific background interference.

Other objects and advantages of the invention will become apparent from the ensuing description.

DETAILED DESCRIPTION OF THE INVENTION

Figure 1:
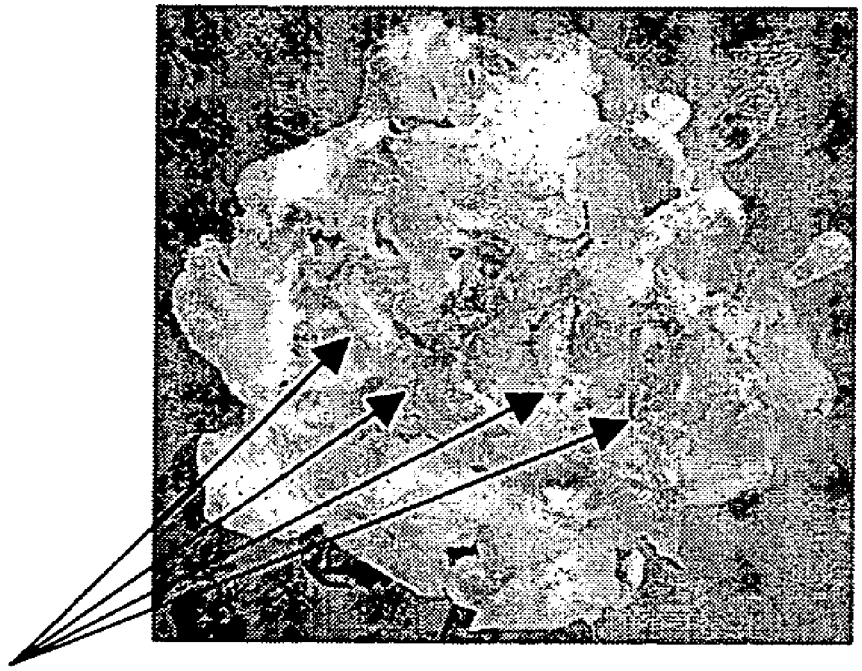
FIG. 1 is a photographic image of a bone fragment contaminated diced chicken sample of Example 1.

The process of this invention may be used for detecting bones, bone fragments, and shell fragments on or near the surface of animal flesh, particularly processed flesh, such as ground meats, fish, or shellfish, and cut meats, most particularly diced (including minced) meats, fish, or shellfish. It is understood that the term processed flesh (or processed animal flesh) as used herein encompasses products which may contain minor (i.e., less than 50%, by weight) of non-flesh animal parts such as fat, cartilage, and organs. Moreover, the invention may detect both the inner and outer surfaces of bone fragments, and thus the orientation of the bone fragments on the flesh is of no significance. The invention is particularly applicable to the detection of bones, bone fragments, and shell fragments on or near the surface of the animal flesh of wild or domestic meat producing animals, including but not limited to poultry, bovine, porcine, ovine, caprine, and ratites, especially cattle and calves, hogs, chickens, turkeys, sheep, and goats, as well as fish and shellfish.

De-boning or shelling of meats, fish, and shellfish is typically conducted at one or more stations along a processing or conveyor line. This de-boned or shelled product may be packaged for consumption "as is", or it may be further processed such as by dicing or grinding, which may be optionally followed by reconstruction into patties, sticks, cakes, or, in the case of fish and shell-fish, textured surimi-like products. A variety of optional fillers, spices, or other ingredients may be added during or after grinding or dicing. The process of the instant invention may be implemented to detect bones, bone fragments, or shell fragments at any time following the de-boning or shelling operation. However, because the invention is ideally suited to detect bones, bone fragments or shells on or near the surface of the product, wherein "near" is defined herein to generally refer to within approximately 1-5 mm of the surface exposed to illuminating light, the invention is preferably used to examine de-boned or shelled product prior to the above-mentioned reconstruction. The actual depth to which bones or bone or shell fragments may be detected will vary with the transparency of the flesh to the wavelengths of light used. Examination in this manner will minimize or eliminate the number of embedded bone or shell fragments which might escape detection.

Detection of bones, bone fragments, and shell fragments in accordance with this invention is based upon applicants' discovery that these materials may be more clearly differentiated from the flesh of their source animal (i.e., the background) when fluorescent light emissions are measured at two selected wavelengths, and the ratio or subtractive difference of the intensity of the fluorescence at these wavelengths is calculated. Whereas the wavelength of the irradiating light is generally not critical, and need only be effective to elicit fluorescence of the animal's bones or shells, in contrast, the selection of the appropriate emission wavelengths is critical. For the purposes of this invention, the first and second different wavelengths are selected to yield a substantial difference between the subsequently calculated ratio or subtractive difference for bones or shells, versus the corresponding ratio or subtractive difference for animal flesh. Although the use of ratio values is generally preferred, the skilled practitioner will recognize that the use of subtractive differences may be substituted with little or no loss in accuracy. As used herein, the ratio is calculated as the corresponding value of the fluorescent light emission intensity measured at the first wavelength divided by the measured value of the intensity at the second wavelength, and the subtractive difference is calculated as the corresponding value of the fluorescent light emission intensity measured at the first wavelength minus the measured value of the intensity at the second wavelength (or the inverse thereof). For brevity, the generic term "comparison value" is defined herein to refer to either the ratio or the subtractive difference. The skilled practitioner will recognize that there are a variety of techniques to maximize the statistical difference between the comparison values.

In general, the two wavelengths should be selected to emphasize the difference between the slope of the line connecting the measured fluorescent intensity values for bones or shells at the two wavelengths, and the corresponding slope of the line determined for animal flesh. If the spectra for bones or shells, and the spectra for flesh, cross at some wavelength, then a good choice for the first wavelength is the wavelength where the absolute difference in the magnitude of the spectra for bones or shells, and for flesh, is greatest. The second wavelength should then be the wavelength where the difference between spectra for bones or shells, and flesh, is the greatest magnitude where the difference has the opposite sign as the difference for the first wavelength. A variety of wavelengths are suitable for use for measurement of the first and second fluorescent emissions. Without being limited thereto, in the preferred embodiment the first wavelength, which is greater than the second wavelength, is between about 450 to about 650 nm, most preferably about 620 nm, while the second wavelength is preferably between about 400 to about 600 nm, more preferably between about 435 to about 535 nm or between about 550 to about 600 nm, most preferably about 460, 510, or 575 nm. A variety of irradiating wavelengths are suitable for eliciting fluorescence from the bones or shells, and include but are not limited to between about 280 to about 500 nm, preferably between about 340 to about 400 nm.

Following the measurement of the fluorescent light emissions, the comparison value of the fluorescent light emission intensities measured at the first and second wavelengths is calculated, and the presence or absence of bones, bone fragments, or shell fragments on the animal flesh is determined from this comparison value. As used herein, it is understood that the term "ratio of the fluorescent light emission intensities measured at the first and second wavelengths" includes the ratio of the intensity at the first wavelength to the intensity at the second wavelength, and the inverse thereof. Similarly, the term "subtractive difference of the fluorescent light emission intensities measured at the first and second wavelengths" includes the value of the fluorescent light emission intensity measured at the first wavelength minus the measured value of the intensity at the second wavelength, and the inverse thereof. As described in greater detail hereinbelow, the determination or identification of the presence of bones, bone fragments, or shell fragments from the comparison value may be effected using a variety of techniques, and the particular technique selected is not critical. Moreover, the process of the invention described above provides an accurate indication of the presence of contaminating bones, bone fragments, or shells at the location on the animal flesh where the fluorescence emissions are measured. Thus, the analysis should be repeated at a plurality of locations across the animal tissue being examined.

Figure 4A:
FIGS. 4a and 4b are ratio images prepared from the ratio of the measured fluorescence at 620 nm/510 nm, and at 620/575 nm, respectively.
Figure 4B:

In a first preferred embodiment, the determination of the presence of bones, bone fragments, or shell fragments from the ratio is effected by generation of a ratio image (also referred to as a two band ratio image) such as shown in FIGS. 4a and 4b. The general technique for the generation of ratio images is described in detail in Lefcourt et al. [2003. Automated detection of fecal contamination of apples by multispectral laser-induced fluorescence imaging. Applied Optics. 42(19):3935-3943] or Kim et al. [2004. Uses of hyperspectral and multispectral laser induced florescence imaging techniques for food safety inspection. Key Engineering Materials. vols. 270-273, pages 1055-1063], the contents of each of which are incorporated by reference herein. In brief, the fluorescence emissions at the first and second wavelengths are measured at a plurality of positions on the sample of animal flesh such as from one or more images collected from the illuminated sample. In the case of digital images collected simultaneously or sequentially at the first and second wavelengths, the intensity of the emissions at each wavelength may be measured at each pixel or predetermined groups of pixels of the image. The ratio of the intensities at the different wavelengths may be calculated at each position or pixel, and then linearly scaled or transformed into the ratio image using conventional techniques. As shown in FIGS. 4a and 4b, bone fragments are readily discernible from the surrounding flesh by the naked eye in the enhanced images.

In an alternative preferred embodiment, the presence or absence of bones, bone fragments, or shell fragments from the ratios is determined by comparison of the calculated comparison value to a predetermined threshold value of the comparison value. This threshold will vary with the desired level of selectivity, the particular wavelengths used, the measuring equipment, and the specific animal tested, and may be readily determined by a practitioner skilled in the art by routine experimentation. The selection of a detection threshold is dependent on image transforms used prior to detection, which include but are not limited to image normalization. Thresholds can be determined by subjective assessment or a variety of standard statistical techniques. Typically, the threshold will be determined by measuring the ratio (or subtractive difference) of a negative control (bone-free) sample of the same type of animal flesh measured at substantially the same said first and second wavelengths. The comparison of the calculated ratio values (or subtractive differences) (obtained from measurements of the animal flesh product) with the threshold value will depend upon how the first and second wavelengths are selected. Specifically, if the wavelengths are selected such that the comparison value for bone is greater than the comparison value for flesh, then any calculated comparison value which is above the threshold is bone. Conversely, if the wavelengths are selected such that the comparison value for bone is less than the comparison value for flesh, then any calculated comparison value which is below the threshold is bone. In a variation of this embodiment, when the comparison value is calculated at a plurality of positions on the sample of the flesh (or pixels across a digital image of the flesh) the presence and number of adjacent positions or pixels having comparison values which are significantly different from the threshold value may determined, and will provide an indication of the relative size of the bone or bone or shell fragment.

Figure 5A:
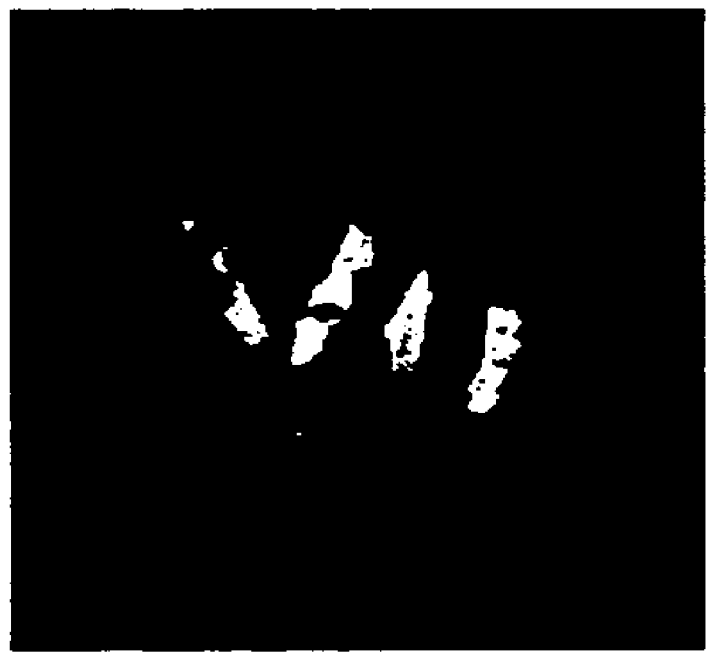
FIGS. 5a and 5b are binary classification images prepared from the ratio images of FIGS. 4a and 4b, respectively, as described in Example 1.
Figure 5B:

In another alternative preferred embodiment, a binary classification image such as shown in FIGS. 5a and 5b may be prepared, also as described by Lefcourt et al. (2003) or Kim et al. (2004), ibid. In this embodiment, the comparison value of the intensities at the different wavelengths may be calculated at each position or pixel as in the preparation of the above-mentioned ratio image, and then each calculated comparison value is compared to the above-mentioned threshold value. Each comparison value which is less than or equal to this threshold is assigned a first color, such as black, while each comparison value which is greater than the threshold is assigned a second, contrasting color, such as white. It is understood that the handling of situations where the calculated comparison value at a given position or pixel is equal to the threshold value is an arbitrary decision. A binary classification image may then be generated from these color values at their respective positions or pixels. In this image, bones or bone or shell fragments will be shown as one color (such as white) while flesh is shown by the other color (in this case, black).

Upon determination of the presence of bone or bone or shell fragments, a number of responses may be initiated. For instance, the detection of bones or bone or shell fragments may trigger one or more audible or visible signals alerting the appropriate production worker who may then manually remove the product from the conveyor line or simply remove bone or fragments, or the suspect product may be automatically removed from the line. The detection of bones or bone or shell fragments on the product may also allow the processor to adjust and improve upstream processing steps in order to prevent contamination wherever possible and improve quality. In the instance where the size of the bone, bone fragment, or shell fragment is determined as described above, the decision to remove a product from the line may be dependent upon detection of a minimum size.

The apparatus for measuring the fluorescence emissions is not critical. In a first embodiment, a multispectral laser-induced fluorescence imaging system (MLIFIS) is used, such as described in Kim et al. [2003, Multispectral laser induced fluorescence imaging system for large biological samples. Applied Optics. 42(19):3927-3934], the contents of which are incorporated by reference herein. This system incorporates pulsed lasers with a short pulse duration and a fast-gated detection system synchronized to the laser pulses to allow capture of the fluorescent light emissions in ambient light. Moreover, this system also allows the simultaneous acquisition of multispectral images, currently at 4 different wavelengths, including the desired first and second wavelengths. Thus, up to three different ratios could be determined simultaneously. In brief, the MLIFIS includes a pulse laser as the illumination source, a beam expander, a lens, a common-aperture adapter, and a fast-gated intensified camera. A microprocessor based control unit having conventional interface hardware may be provided for receiving and interpreting the signals from the camera, and manipulating data and/or generating images as described above. An audible or visible signal generator may be provided in communication with the microprocessor, and the microprocessor may also be used for automated control of testing, including automated scanning of samples on a conveyor line, identifying samples positive for bone or bone or shell fragments, and directing the same from the conveyor line.

In an alternative embodiment, the measurements may also be conducted using a multispectral steady state fluorescence imaging system (MFIS). This system incorporates UV fluorescent lamps as the excitation source and an intensified CCD camera equipped with an integral filter wheel to allow sequential capture of emission images at the first and second wavelengths. A microprocessor for data manipulation, image generation, and control as described above is also provided. However, because this system is not capable of operation in ambient light, all measurements should be conducted in a light-tight closed container.

The following examples are intended only to further illustrate the invention and are not intended to limit the scope of the invention which is defined by the claims.

EXAMPLE 1

Figure 2:
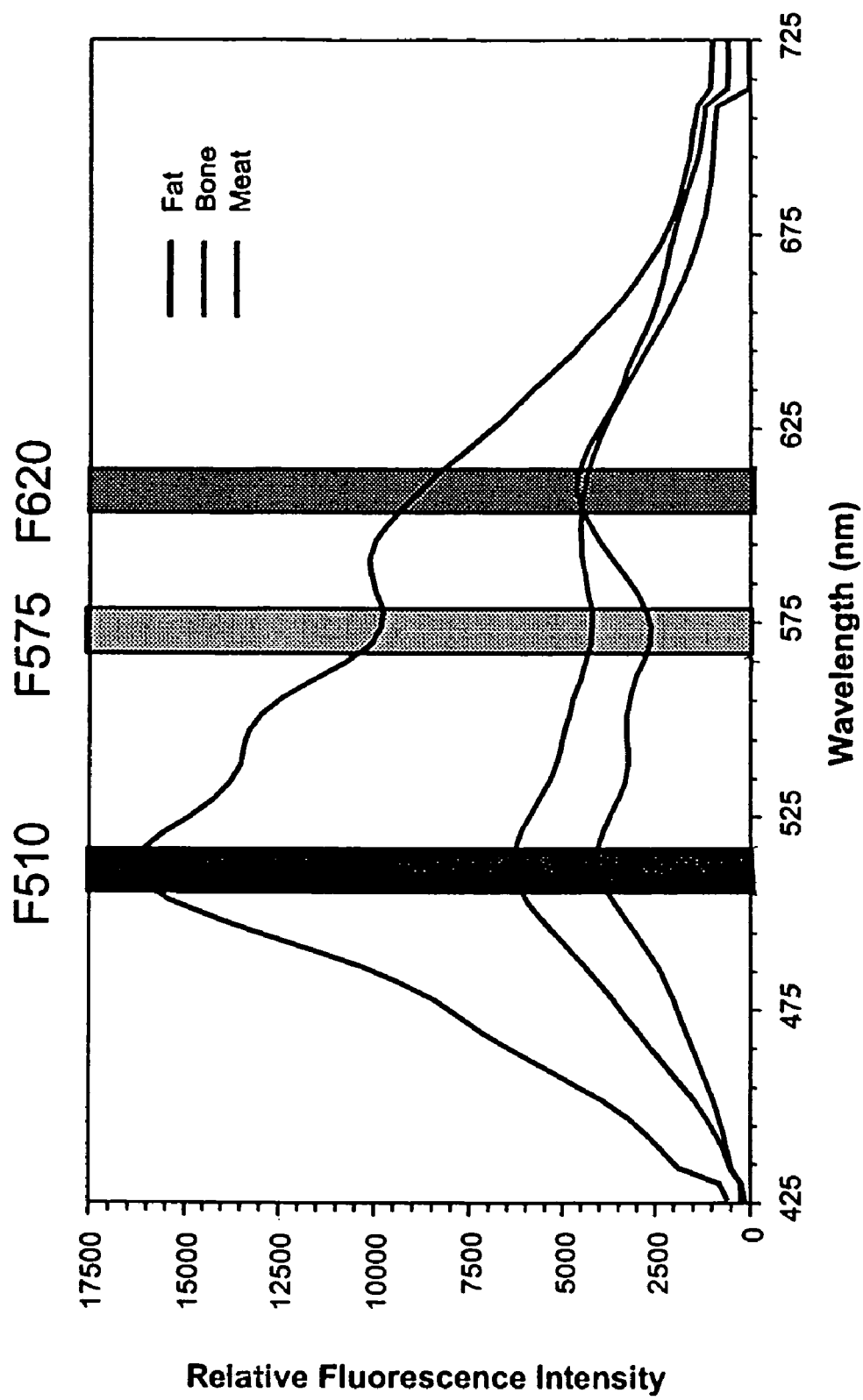
FIG. 2 is the emission spectrum of bone fragment contaminated diced chicken samples of Example 1.
Figure 3A:
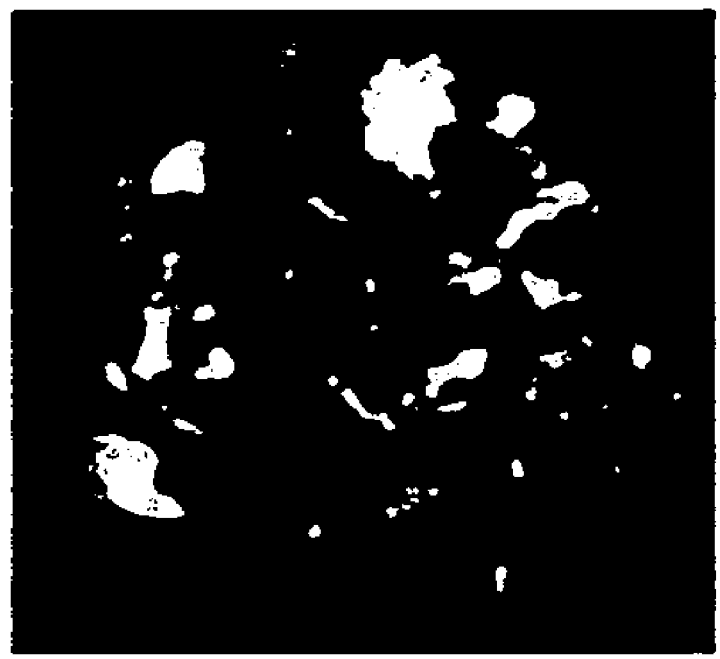
FIGS. 3a, 3b, and 3c are fluorescent images of the bone fragment contaminated diced chicken sample of FIG. 2 measured at 510, 575, and 620 nm, respectively.
Figure 3B:
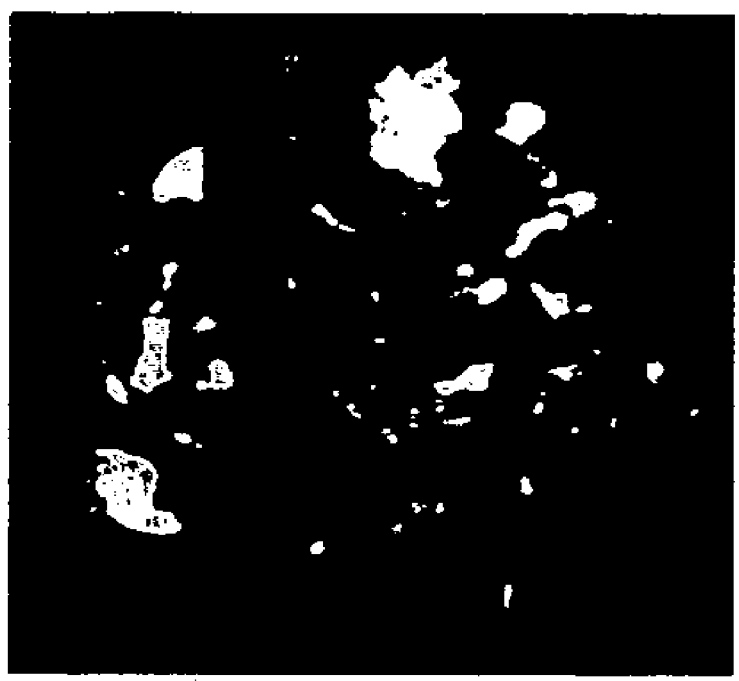
Figure 3C:

Various chicken meat portions (dark and white meats including fats) were diced and mixed randomly and placed approximately 1 cm thick on a nonfluorescent plate. Chicken leg, thigh and wing bones were cracked using a hammer to create bone fragments. Bone fragments were placed on top of the chicken meats such that both inner and outer surfaces of the bone fragments were exposed (FIG. 1). Hyperspectral fluorescence and reflectance images of the samples were acquired using a multispectral laser-induced fluorescence imaging system (MLIFIS), such as described in Kim et al. (2002, ibid) or Kim et al. [2003, Applied Optics, ibid). Samples were exposed to an excitation wavelength of approximately 360 nm, and fluorescence emissions were collected at 510, 575, and 620 nm. The emission spectra and fluorescence images at 510, 575, and 620 nm are shown in FIGS. 2 and 3. Ratio images were calculated from ratios of the fluorescence emissions at 620 nm/510 nm and at 620 nm/575 nm, as were the corresponding binary classification images. The results are shown in FIGS. 4a and 4b, and 5a and 5b, respectively.

The results demonstrate that fluorescence images provide a means to detect bone fragments regardless of whether the inner or outer surfaces of bone fragments were exposed. Fluorescence emissions form the various meat and bone fragments exhibit multiple emission peaks from approximately 400 to 650 nm. The critical finding is the use of two-band ratios (e.g., fluorescence band in the 400 to 600 nm ratio'd to 600-650 nm band) significantly enhanced the ability to detect the exposed bone fragments.

It is understood that the foregoing detailed description is given merely by way of illustration and that modifications and variations may be made therein without departing from the spirit and scope of the invention.

We claim:

1. A method for detecting bones, bone fragments, and shell fragments on or near the surface of animal flesh during processing comprising:
   a. illuminating the surface of a product comprising animal flesh with UV or visible light having a wavelength effective to elicit fluorescence of animal bones or shells,
   b. measuring the intensity of fluorescent light emissions from said surface at first and second wavelengths, wherein said first and second wavelengths are selected to yield a substantial difference between the ratio or subtractive difference for bones or shells, and the ratio or subtractive difference for animal flesh, wherein said ratio is the ratio of said fluroescent light emission intensities measured at said first and second wavelengths and said subtractive difference is the mathematical difference between said fluorescent light emission intensities measured at said first and second wavelengths, c. calculating a comparison value of said fluroescent light emission intensities measured at said first and said second wavelengths, wherein said comparison value comprises the ratio of said fluroescent light emission intensities measured at said first and said second wavelengths or subtractive difference between said fluorescent light emission intensities measured at said first and said second wavelengths, and d. determining the presence or absence of bones, bone fragments, or shell fragments from said comparison value.

2. A method as described in claim 1 wherein said animal flesh is selected from the group consisting of bovine, poultry, porcine, ovine, caprine, ratite, fish, shellfish.

3. The method of claim 1 wherein said product comprises ground animal flesh or diced animal flesh.

4. The method of claim 3 wherein said animal flesh is selected from the group consisting of bovine, poultry, porcine, ovine, caprine, ratite.

5. The method of claim 3 wherein said animal flesh comprises poultry.

6. The method of claim 3 wherein said animal flesh is selected from the group consisting of fish and shellfish.

7. The method of claim 1 wherein said fluroescent light emissions at said first and second wavelengths are measured at a plurality of different, discrete positions on said surface of said product, and said comparison value is calculated at each said position.

8. The method of claim 7 further comprising determining any said position wherein said comparison value is indicative of the presence of bones, bone fragments, or shells.

9. The method of claim 1 wherein said measuring of said fluroescent light emissions at said first and second wavelengths comprises acquiring a digital image of said product.

10. The method of claim 9 wherein said fluorescent light emissions at said first and second wavelengths are measured at a plurality of discrete positions of said digital image, and said comparison value is calculated at each said position.

11. The method of claim 10 further comprising generating a second image of said product from each said comparison value calculated at each said position, wherein the presence of bones, bone fragments, or shells, on or near the surface of said product are visually discernible in said second image.

12. The method of claim 1 wherein said determining comprises determining if said comparison value is significantly different from a threshold value of the comparison value for a control animal flesh measured at substantially the same said first and second wavelengths.

13. The method of claim 12 wherein said fluorescent light emissions at said first and second wavelengths are measured at a plurality of different, discrete positions on said surface of said product, and said comparison value is calculated at each said position.

14. The method as described in claim 1 further comprising transporting said product on a conveyor line, and further wherein said illuminating, measuring, calculating, and determining are conducted while said product is transported on said conveyor line.

15. The method of claim 14 further comprising removing said product from said conveyor line if said comparison value is indicative of the presence of said bones, bone fragments, or shells.

16. The method of claim 14 further comprising removing bones, bone fragments, or shells from said product if said comparison value is indicative of the presence of said bones, bone fragments, or shells.

17. The method of claim 1 wherein said illuminating comprises illuminating said surface with light having a wavelength between about 280 to about 400 nm.

18. The method of claim 17 wherein said illuminating comprises illuminating said surface with light having a wavelength between about 340 to about 360 nm.

19. The method of claim 1 wherein first wavelength is between about 450 to about 650 nm, and said second wavelength is between about 400 to about 600 nm, and said first wavelength is greater than said second wavelength.

20. The method of claim 19 wherein said second wavelength is selected from the group consisting of between about 435 to about 535 nm and between about 450 to about 600 nm.

21. The method of claim 20 wherein said second wavelength is selected from the group consisting of about 460 nm, about 510 nm, and about 575 nm.

22. The method of claim 20 wherein said first wavelength is about 620 nm.

* * * * *